United States Patent
Tsuda et al.

(10) Patent No.: US 6,676,809 B1
(45) Date of Patent: Jan. 13, 2004

(54) PROCESS FOR REMOVAL OF HYDROGEN FLUORIDE

(75) Inventors: Takehide Tsuda; Takeo Matsumoto; Yoshinori Tanaka; Satoshi Komatsu; Satoshi Koyama, all of Osaka (JP)

(73) Assignee: Daikin Industries Ltd., Osaka (JP)

( * ) Notice: Subject to any disclaimer, the term of this patent is extended or adjusted under 35 U.S.C. 154(b) by 0 days.

(21) Appl. No.: 08/967,539

(22) Filed: Nov. 12, 1997

Related U.S. Application Data

(60) Continuation of application No. 08/586,217, filed on Jan. 16, 1996, now abandoned, which is a division of application No. 08/162,010, filed as application No. PCT/JP93/00455 on Apr. 9, 1993, now Pat. No. 5,523,015.

(30) Foreign Application Priority Data

| Feb. 7, 1992 | (JP) | ............................................. 4-107656 |
| Apr. 13, 1992 | (JP) | ............................................... 4-92667 |

(51) Int. Cl.$^7$ ......................... B01D 3/36; C07C 17/386
(52) U.S. Cl. ......................... 203/67; 203/91; 423/481; 510/408; 570/178
(58) Field of Search ............................ 203/39, 91, 67; 423/481, 486; 252/60; 510/408; 570/177, 178

(56) References Cited

U.S. PATENT DOCUMENTS

| 2,450,414 A | * | 10/1948 | Benning | ........................ 202/51 |
| 2,744,148 A |   | 5/1956 | Rub et al. | |
| 3,400,077 A |   | 9/1968 | Orfeo et al. | ................. 252/171 |
| 3,490,739 A |   | 1/1970 | Buckman et al. | ............. 252/60 |
| 3,728,268 A |   | 4/1973 | Burt | ............................ 252/170 |
| 3,789,004 A |   | 1/1974 | McMillan et al. | ........... 252/171 |
| 3,947,558 A | * | 3/1976 | Van Eijl | ....................... 203/80 |
| 4,020,112 A |   | 4/1977 | Boswell, Jr. et al. | ... 260/612 R |
| 4,169,807 A |   | 10/1979 | Zuber | ........................... 252/171 |
| 4,911,792 A |   | 3/1990 | Manzer et al. | ................ 203/39 |
| 4,950,364 A |   | 8/1990 | Wismer | ........................ 203/50 |
| 4,975,156 A |   | 12/1990 | Wismer | ........................ 203/39 |
| 5,196,616 A | * | 3/1993 | Lee et al. | .................... 570/178 |
| 5,211,817 A | * | 5/1993 | Adams et al. | .............. 570/178 |
| 5,707,497 A | * | 1/1998 | Galland et al. | ............. 570/178 |

FOREIGN PATENT DOCUMENTS

| CA | 2026825 A1 | | 4/1991 |
| CA | 1325995 C | | 1/1994 |
| EP | 403108 | * | 12/1990 |
| EP | 0669303 B1 | | 10/1997 |
| JP | 225131 | * | 12/1984 |
| JP | 13726 | * | 1/1985 |
| JP | 733691 | | 2/1995 |
| WO | WO91/04955 A1 | | 4/1991 |
| WO | 12563 | * | 5/1995 |

OTHER PUBLICATIONS

Zh. Prikl. Chim., V. 68, N. 8, 1995, pp. 1395–1397.
Robert H. Perry et al., "Chemical Engineer's Handbook", fifth edition, International Student Edition, pp. 13–36, 13–37.
Lee & Kim, "Vapor–Liquid Equilibria for Hydrogen Fluoride + Difluoromethane, +1, 1, 1, 2–Tetrafluoroethane, and +1–Chloro–1,2,2,2–tetrafluoroethane at 283.3 and 298.2 K", J. Chem. Eng. Data (1996), pp. 41, 43–46.

(List continued on next page.)

*Primary Examiner*—Virginia Manoharan
(74) *Attorney, Agent, or Firm*—Birch, Stewart, Kolasch & Birch, LLP

(57) ABSTRACT

Hydrogen fluoride is effectively removed from a mixture of hydrogen fluoride, dichloromethane, chlorofluoromethane and/or difluoromethane by distilling the mixture so that two-component azeotropic mixtures of hydrogen fluoride and dichloromethane, hydrogen fluoride and chlorofluoromethane and hydrogen fluoride and difluoromethane are removed, or by liquid-separating the mixture into an upper liquid phase rich in hydrogen fluoride and a lower liquid phase not rich in hydrogen fluoride before each liquid phase is distilled as described above.

4 Claims, 2 Drawing Sheets

OTHER PUBLICATIONS

Yun Kang, "Vapor–Liquid Equilibria for the Systems Difluoromethane + Hydrogen Fluoride, Dichlorodifluoromethane + Hydrogen Fluoride, and Chlorine + Hydrogen Flouride", J. Chem. Eng. Data (1998), pp. 43, 13–16.

Amparo Galindo et al., "Predicting the Phase Equilibria of Mixtures of Hydrogen Fluoride with Water, Difluoromethane (HFC–32), and 1, 1, 1, 2–Tetrafluoroethane (HFC–134a) Using a Simplified SAFT Approach", J. Phys. Chem. B. (1997), pp. 2082–2091.

Ela–Study on the HF/R–32 system carried out by Allied Signal Inc. in 1996.

Elb–Study on the HF/R–32 system carried out by Allied Signal Inc. in 1974.

* cited by examiner

PROCESS FOR REMOVAL OF HYDROGEN FLUORIDE

This application is a continuation of application Ser. No. 08/586,217 filed on Jan. 16, 1996, abandoned, which is a divisional of application Ser. No. 08/162,010 filed Dec. 9, 1993, now U.S. Pat. No. 5,523,015, which is a 371 of PCT/JP93/00455 filed Apr. 9, 1993.

BACKGROUND OF THE INVENTION

1. Field of the Invention

The present invention relates to an azeotropic mixture consisting essentially of hydrogen fluoride (hereinafter, referred to as "HF") and dichloromethane (hereinafter, referred to as "R-30"), an azeotropic mixture consisting essentially of HF and chlorofluoromethane (hereinafter, referred to as "R-31") and an azeotropic mixture consisting essentially of HF and difluoromethane (hereinafter, referred to as "R-32"), and a process for the removal of HF from a mixture comprising HF and R-30, R-31 and/or R-32.

R-32 is focused on as a substitute cooling medium for chlorodifluoromethane, and R-30 and R-31 are starting materials for the production of R-32.

2. Description of the Related Art

R-30, R-31 and/or R-32 are conventionally produced by reacting a chlorinated hydrocarbon such as R-30 with HF. Hitherto, a process has been employed in which HF is removed by washing the mixture produced by the reaction and unreacted materials comprising HF, R-30, R-31 and R-32 with an aqueous phase. This process is not so effective because an large amount of an alkali is required to neutralize the washing aqueous solution, and also because a waste from the neutralization has to be treated.

SUMMARY OF THE INVENTION

The present invention provides a process to concentrate or remove HF or other components by forming an azeotropic mixture of HF and R-30, R-31 or R-32 and optionally utilizing liquid separation of a mixture of HF and R-30 and/or a mixture of HF and R-31 into an upper liquid phase and a lower liquid phase under certain conditions.

BRIEF DESCRIPTION OF THE DRAWINGS

In FIG. 1, the numeral 11 indicates a starting mixture stream, 12 indicates a stream of R-31, 13 indicates a feed stream, 14 indicates a distillation apparatus, 15 indicates a distillate stream, 16 indicates a reflux stream and 17 indicates a bottom product stream.

In FIG. 2, the numeral 21 indicates a liquid-liquid separation apparatus, 23 indicates a distillation apparatus, 25 indicates a distillate stream, 27 indicates a reflux stream, 29 indicates a bottom product stream, 31 indicates a cooler, 33 indicates a distillation apparatus, 35 indicates a distillate stream, 37 indicates a reflux stream, 39 indicates a bottom product stream and 41 indicates a cooler.

DETAILED DESCRIPTION OF THE INVENTION

Figure 1:
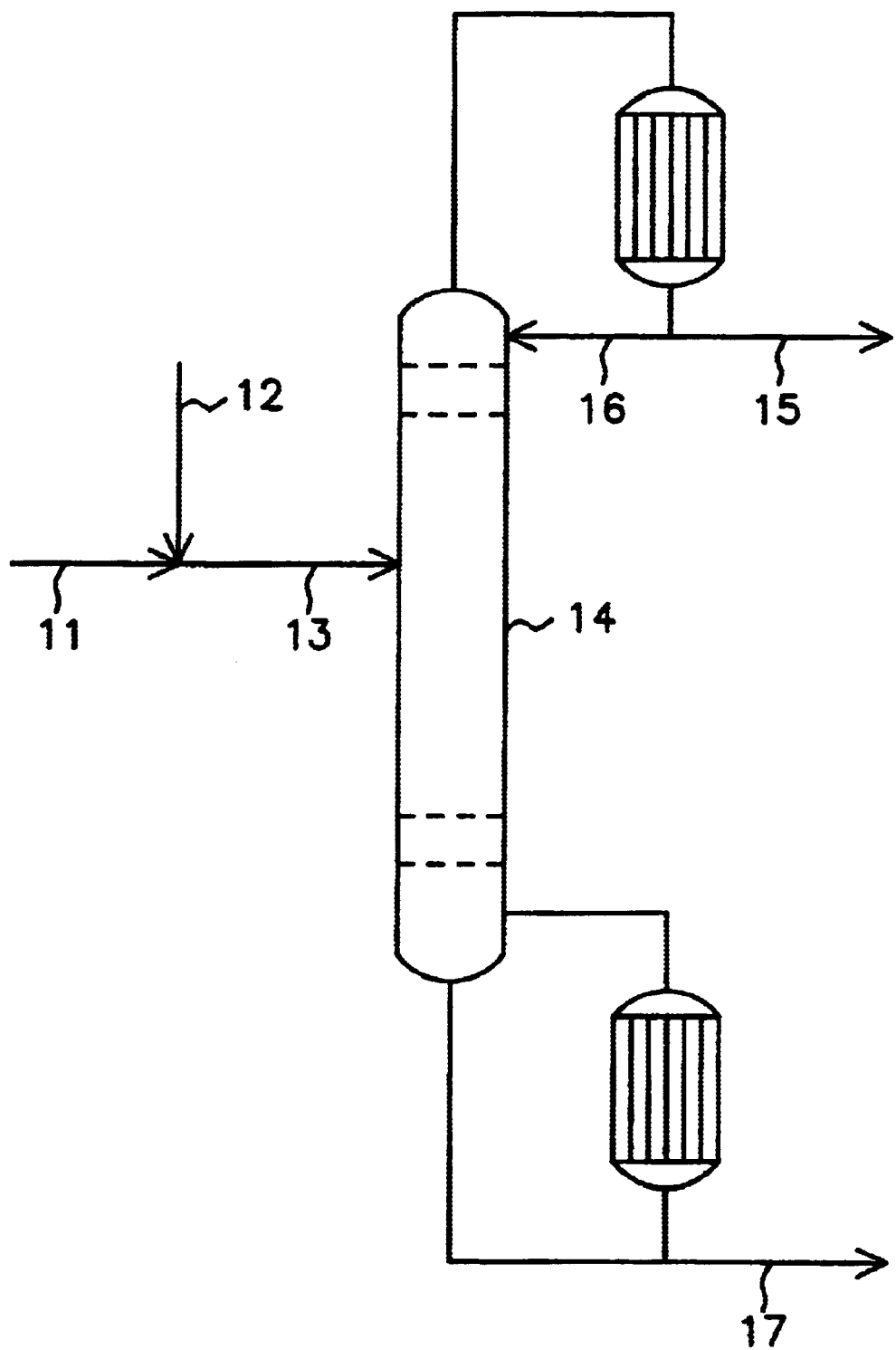
FIG. 1 shows a process flow sheet of one embodiment in which HF is removed according to the present invention.

The present inventors have made intensive studies on the process to remove HF from a mixture comprising HF and R-30, R-31 and/or R-32, so that it has been found that the combinations of HF and R-30, HF and R-31 and HF and R-32 each set of the compounds forms an azeotropic mixture having a minimum boiling point, respectively, and thus the present invention has been made. These mixtures can be used as refluxes in distillation operations in which HF is removed from a mixture comprising HF and R-30, R-31 and/or R-32, whereby effective separation is achieved.

In the first aspect, the present invention provides an azeotropic mixture consisting essentially of HF and R-30, an azeotropic mixture consisting essentially of HF and R-31 and an azeotropic mixture consisting essentially of HF and R-32. These mixtures have boiling points at atmospheric pressure of about 12° C., about −11° C., and about −53° C., respectively.

In the second aspect, the present invention further provides a process for the concentration or the removal of any one of the components of the azeotropic mixtures by using the azeotropic phenomena.

The terms "concentration" and "removal" herein used are intended to mean relative concepts. That is, the concentration of one component in a mixture means the removal of other components in the mixture rather than said one component.

Namely, by distilling a mixture comprising HF and R-30, the azeotropic mixture of HF and R-30 is removed from the original mixture so that R-30 substantially free from HF or HF substantially free from R-30 is obtained, so that the process for the concentration or the removal of R-30 or HF is provided.

In addition, by distilling a mixture comprising HF and R-31, the azeotropic mixture of HF and R-31 is removed from the original mixture so that R-31 substantially free from HF, or HF substantially free from R-31 is obtained, so that the process for the concentration or the removal of R-31, or HF is provided.

Further, by distilling a mixture comprising HF and R-32, the azeotropic mixture of HF and R-32 is removed from the original mixture so that R-32 substantially free from HF or HF substantially free from R-32 is obtained, so that the process for the concentration or the removal of R-32 or HF is provided.

Further, when the above processes are combined, the present invention provides a process of removing or concentrating HF in which a mixture comprising HF and R-30, R-31 and/or R-32 is distilled so that HF or other component is removed from the mixture as the azeotropic mixture of HF and R-30, the azeotropic mixture of HF and R-31 and/or the azeotropic mixture of HF and R-32, whereby R-30, R-31 and/or R-32 substantially free from HF or HF substantially free from R-30, R-31 and/or R-32 is produced. The pressure during distillation of the mixture is in the range of 0.5 Kg/cm$^2$-abs to 30 Kg/cm$^2$-abs.

As described above, the two-component systems of HF and R-30, HF and R-31, and HF and R-32 each has the azeotropic mixture having the minimum boiling point. These azeotropic mixtures have been found by the present inventors for the first time.

It has been found that when the mixture of HF and R-30 is distilled under atmospheric pressure, HF cannot be further concentrated above a HF/R-30 molar ratio of about 86/14 (an azeotropic point in this case is 12° C.). In other words, a liquid phase having such a molar ratio is equilibrium with a vapor phase having the same molar ratio as that of the liquid phase. The azeotropic composition of HF and R-30 varies with a pressure, and the HF/R-30 molar ratio is about 80/20 at a pressure of 3.0 Kg/cm²G and about 77/23 at a pressure of 15 Kg/cm2G.

In addition, it has been found that when the mixture of HF and R-31 is distilled under atmospheric pressure, R-31 cannot be further concentrated above a HF/R-31 molar ratio of about 22/78 (an azeotropic point in this case is -11° C.). In other words, a liquid phase having such a molar ratio is in equilibrium with a vapor phase having the same molar ratio as that of the liquid phase. The azeotropic composition of HF and R - 31 varies with a pressure, and the HF/R-31 molar ratio is about 20/80 at a pressure of 5.8 Kg/cm²G and about 19/81 at a pressure of 15 Kg/cm²G.

Further, it has been found that when the mixture of HF and R-32 is distilled under atmospheric pressure, R-32 cannot be further concentrated above a HF/R-32 molar ratio of about 1.2/98.8 (an azeotropic point in this case is –53° C). In other words, a liquid phase having such a molar ratio is in equilibrium with a vapor phase having the same molar ratio as that of the liquid phase. The azeotropic composition of HF and R-32 hardly varies with a pressure.

HF can be removed from the mixture of HF and R-30 by directly distilling it using a distillation apparatus. Since it has been found that HF and R-30 forms an azeotropic mixture, HF substantially free from R-30 can be effectively obtained from a bottom of the distillation apparatus when a composition of R-30 in the mixture is smaller than the composition of R-30 of the azeotropic mixture and the azeotropic mixture of HF and R-30 is used as a reflux stream returned to the distillation apparatus.

To the contrary, when the composition of R-30 of the mixture is larger than the composition of R-30 that of the azeotropic mixture and the azeotropic mixture of HF and R-30 is used as the reflux steam, R-30 substantially free from HF can be effectively obtained from the bottom of the apparatus.

In addition, HF is removed from the mixture of HF and R-31 by directly distilling it using a distillation apparatus. Since it has been found that HF and R-31 forms the azeotropic mixture, R-31 substantially free from HF can be effectively obtained from a bottom of the distillation apparatus when a composition of R-31 in the mixture is larger than the composition of R-31 of the azeotropic mixture and the azeotropic mixture of HF and R-31 is used as a reflux stream.

To the contrary, when the composition of R-31 of the mixture is smaller than the composition of R-31 of the azeotropic mixture and the azeotropic mixture of HF and R-31 is used as the reflux steam, HF substantially free from R-31 can be effectively obtained from the bottom of the apparatus.

Further, HF is removed from the mixture of HF and R-32 by directly distilling it using a distillation apparatus. Since it has been found that HF and R-32 forms the azeotropic mixture, R-32 substantially free from HF can be effectively obtained from a bottom of the distillation apparatus when a composition of R-32 in the mixture is larger than the composition of R-32 of the azeotropic mixture and the azeotropic mixture of HF and R-32 is used as a reflux stream.

To the contrary, when the composition of R-32 of the mixture is smaller than the composition of R-32 of the azeotropic mixture and the azeotropic mixture of HF and R-32 is used as the reflux steam, HF substantially free from R-32 can be effectively obtained from the bottom of the apparatus.

The apparatus which is used for the above azeotropic distillation operations may be any one which can be used in a conventional distillation operation. When a purification column such as a tray column or a packed column is used, especially preferable results are obtained. Distillation operation may be carried out batch-wise or continuously.

The present invention is the most useful for the removal of HF from a reaction mixture comprising R-31 and R-32 produced from R-30 by liquid or vapor phase fluorination with HF in the presence of a catalyst and also comprising unreacted HF and R-30. The most preferred embodiment of the present invention will be explained below.

A process flow sheet of one embodiment of a separation apparatus is shown in FIG. 1 which is used according to the present invention. Conventionally, a product of the above reaction is withdrawn as a vapor phase. The produced mixture comprising, in addition to R-30, R-31, R-32, HF and hydrogen chloride, a small amount of organic substances. Hydrogen chloride is removed from the mixture beforehand by distillation, whereby, a mixture comprising R-30, R-31, R-32 and HF as main components is obtained. Such a mixture (stream 11) is supplied to the distillation apparatus 14.

In this case, it has been found that when the molar ratio of R-31/HF is larger than four, it is preferable to add R-31 (steam 12) in order to make the molar ratio be larger than four. This is because HF is concentrated at the bottom of the apparatus when R-31/HF is less than four since the azeotropic composition of R-31/HF is about 78/22 at atmospheric pressure. In the distillation apparatus 14, a portion of the distillate of HF and R-32 and/or R-31 azeotropically distilled with HF from the top of the apparatus is returned to the top as the reflux (stream 16). R-30 and/or R-31 substantially free from HF remains at the bottom of the apparatus, which is withdrawn as the bottom product (stream 17). Thus, HF is effectively removed from the mixture.

The above operation is preferably carried out continuously. However, it is possible to carry out.

In the third aspect, the present invention provides a process for the removal of HF from the mixture comprising HF and R-30, R-31 and/or R-32 by means of an operation using a liquid separation. The process utilizes separation of the mixture of HF and R-30 readily into an upper liquid phase rich in HF and a lower liquid phase rich in R-30, and also separation of the mixture of HF and R-31 readily into an upper liquid phase rich in HF and a lower liquid phase rich in R-31 at a temperature of less than –200° C. In addition, the mixture of HF, R-30 and/or R-31 (and optionally included R-32) is also separated into an upper liquid phase rich in HF and a lower liquid phase not rich in HF at a temperature of less than 80° C. A separation operation which carries out the liquid separation allows HF or other component to be concentrated in or removed from the mixture comprising HF and R-30 and/or R-31 (and optionally including R-32).

In the fourth aspect, the present invention provides a process of concentrating or removing one component of the upper liquid phase and/or the lower liquid phase obtained from the liquid separation operation as described above in which it is subjected to a suitable treatment by which at least one component is concentrated or removed preferentially to the other components, such as distillation, extraction, absorption and the like, so that the increased concentration or reduced concentration of said one component of the upper liquid phase and/or the lower liquid phase achieved by the liquid separation operation is further increased or reduced. In this aspect, the azeotropic distillation is the most preferable treatment.

Thus, the present invention provides a process for the concentration or the removal of one component of HF and R-30 which process comprises steps of separating a mixture of HF and R-30 into an upper liquid phase rich in HF and a lower liquid phase rich in R-30 and at least concentrating said one component by means of any suitable treatment such as distillation which removes HF or R-30 preferentially, and preferably removing said one component so that said one component is substantially separated from the other component.

The term "concentration" herein used is intended to mean relative increase in a concentration of one component of a mixture and relative decrease in a concentration of the other component. The term "removal" herein used is intended to mean to relative decrease in a concentration of one component of a mixture and relative increase in a concentration of the other component. Thus, even the treatment of the above liquid separation alone carries out the concentration or removal.

Similarly to the case of R-30 as described above, the present invention provides a process for the concentration or removal of one component of HF and R-31 in which a mixture of HF and R-31 is separated into an upper liquid phase rich in HF and a lower liquid phase rich in R-31, and said one component is at least concentrated by means of any suitable treatment which removes HF or R-31 preferentially, and preferably said one component is substantially separated from the other component.

Thus, in the fourth aspect, the present invention provides a process for the concentration or the removal of at least one component of HF, R-30 and R-31 in which a mixture of HF and R-30 or a mixture of HF and R-31 is liquid-separated into an upper liquid phase and a lower liquid phase, respectively, and the upper liquid phase and the lower liquid phase of each mixture is subjected to distillation operation separately so that HF is distilled off as the azeotropic mixture of HF and R-30 or R-31, whereby depending on the composition of each phase to be subjected to the distillation operation, R-30 free from HF or HF free from R-30, or HF free from R-31 or R-31 free from HF is obtained from a bottom of a distillation column.

In the above case, R-30 and R-31 (and optionally R-31) may be present in the mixture with HF simultaneously. In such a case, the mixture is separated into the upper liquid phase and the lower liquid phase, and each phase is distilled separately so that the azeotropic mixture is distilled from the top of the column as in the above, whereby a mixture of R-30 and R-31 (and optionally R-32) substantially free from HF or HF substantially free from R-30 and R-31 (and optionally R-32) is obtained from the bottom of the column. As described above, R-32 may be present in the mixture, in which case it is sufficient to assume that a portion of R-31 is replaced with R-32 since behavior of R-32 is similar to that of R-31.

The mixture of HF and R-30 readily separates into the lower liquid phase rich in R-30 and the upper liquid phase rich in HF. When the mixture of HF and R-31 is cooled, it separates into the lower liquid phase rich in R-31 and the upper liquid phase rich in HF. That is, simple cooling allows the formation of upper liquid phase rich in at least one component and a lower liquid phase not rich in said at least one component (thus, rich in the other components) when relatively compared with concentrations of the original mixture. When HF is removed from the formed lower liquid phase not rich in HF by a suitable treatment which can effectively remove HF from such a mixture (for example, distillation, extraction, absorption, adsorption neutralization with an alkali and so on), the concentrations of R-30 and R-31 can be further increased. Namely, R-30 or R-31 is concentrated while HF is removed.

To the contrary, the upper liquid phase is rich in HF. Therefore, when the upper layer is subjected to a suitable treatment which can mainly remove R-30 or R-31 such as distillation, extraction, absorption and so on, the concentration of HF can be further increased while R-30 and/or R-31 is removed.

In addition, when a mixture comprising HF, R-30, R-31 and/or R-32 is cooled, it is separated into a lower liquid phase rich in the organic substances of R-30, R-31 and/or R-32 and an upper liquid phase rich in HF. Similarly to the above, a suitable treatment which can effectively remove HF from the lower liquid phase concentrates the organic substances to increase their concentrations while HF is removed. With respect to the upper liquid phase, similar treatment is applicable so that HF is further concentrated.

When the mixture of HF and R-31 is phase-separated by cooling, a temperature not higher than −20° C. is employed. No phase separation phenomenon is not observed at a temperature higher than −20° C. regardless the HF/R-31 ratio of the mixture. A preferred cooling temperature is not higher than −25° C. When the temperature is higher than −25° C., separation may be insufficient since a difference in the composition between the upper liquid phase and the lower liquid phase is small and thus the difference in a specific gravity between the two phases is also small. The minimum cooling temperature is not specifically limited provided that it is higher than a freezing point of R-31 (−133° C.). However, the minimum cooling temperature is not lower than about −50° C. When the cooling temperature is lower than −50° C., much energy is required for cooling and thus uneconomical. The preferable temperature range is from −30° C. to −50° C.

When HF contains R-30 and at least R-31, a preferable temperature for the liquid separation is in the range of from 60° C. to −30° C. Further, when R-32 is contained, the same temperature range is generally preferable.

When the mixture of HF, R-30, R-31 and/or R-32 is cooled, the lower liquid phase rich in the organic compounds and the upper liquid phase rich in HF are obtained depending on the composition of the mixture as a whole. The temperature at which the phase separation occurs depends on the ratio of the organic substances. The more R-30 is present, the higher the temperature at which the separation begins. In the case in which R-30 and HF have the same concentrations, the more R-31 is present, the higher the temperature at which the separation begins, for example about 60° C.

Since HF and R-30, HF and R-31, and HF and R-32 each forms the azeotropic mixture as described above, the removal HF or the organic substances (R-30, R-31 and/or R-32) from the mixture of HF and R-30, R-31 and/or R-32 (such as the lower liquid phase and the upper liquid phase obtained by the liquid separation) can be carried out by the combination of the liquid separation operation with the azeotropic distillation operation. In this case, any distillation apparatus may be used provided that can be used as a conventional distillation operation. Preferable results are obtained when a fractionating apparatus is used such as a tray column, a packed column, and so on. Further, the distillation may be carried out either continuously or batchwise.

The combination described above is the most useful for the removal of HF from a mixture comprising R-31 and R-32 produced from vapor or liquid fluorination of R-30 with HF in the presence of a catalyst and also comprising unreacted HF and R-30. The most preferable embodiment of the present invention will be explained below.

Figure 2:
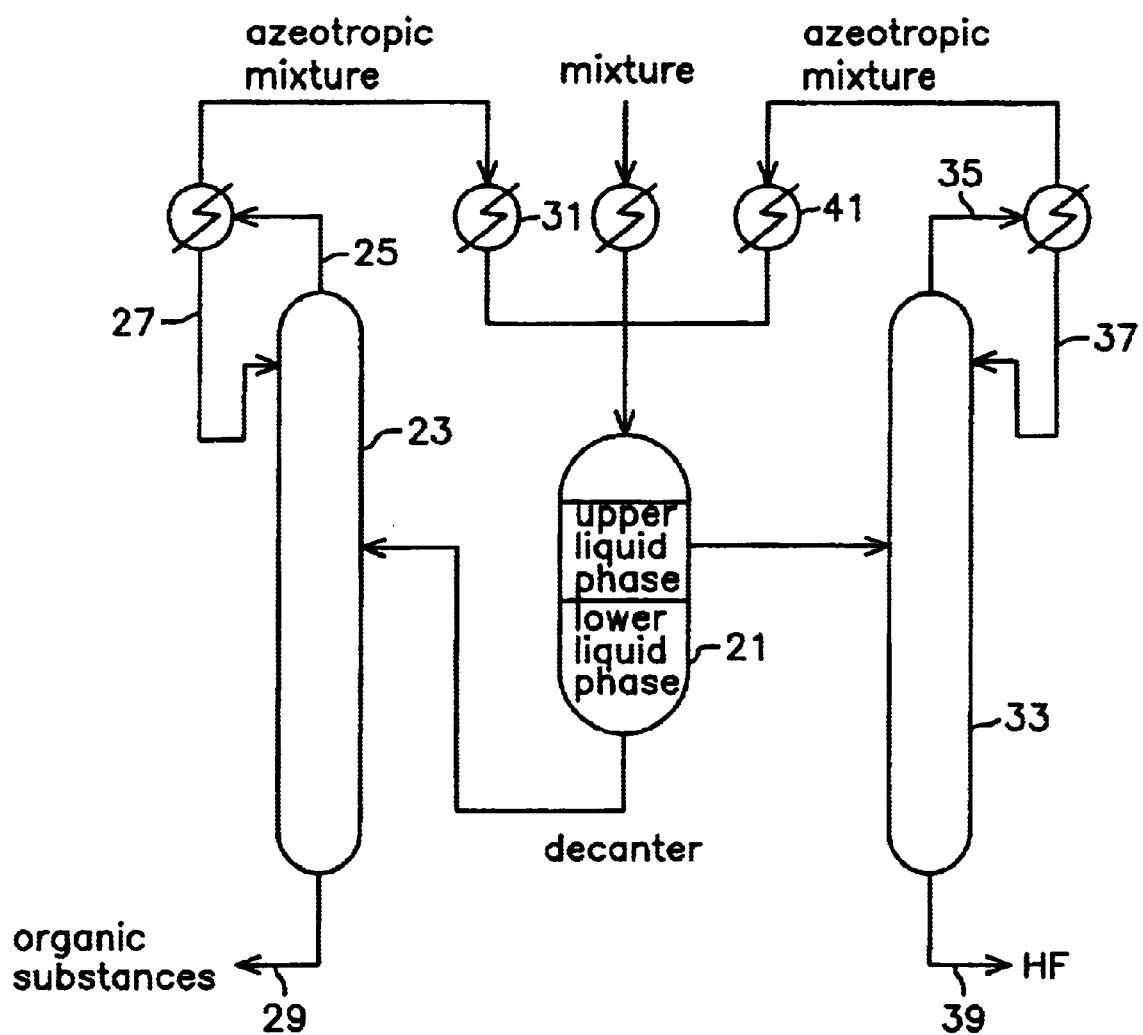
FIG. 2 shows a process flow sheet of another embodiment in which HF is removed according to the present invention.

FIG. 2 shows a process flow sheet of another embodiment in which HF is removed according to the present invention. In the above reaction, the product is usually withdrawn in vapor form. The resulted mixture comprises a small amount of organic compounds in addition to R-30, R-31, R-32, HF and hydrogen chloride. From such a mixture, a mixture mainly comprising R-30, R-31, R-32 and HF is obtained by distilling off hydrogen chloride beforehand, and then cooling to below −20° C. through the cooler. Then, the mixture is supplied to the liquid separation apparatus 21 (such as a liquid-liquid separation apparatus, for example a decanter). An lower liquid phase rich in the organic substances obtained in the liquid separation apparatus is supplied to the distillation apparatus 23 and the azeotropic mixtures 25 of HF and the organic substances are distilled from the top of the apparatus. A portion of the azeotropic mixtures of HF and the organic substances is returned to the top of the distillation apparatus 23 as the reflux stream 27 and the balance is cooled below −20° C. through the cooler 31 and then supplied to the liquid phase separation apparatus 21 and then the above operations are repeated. When repeated, pressure blow off at the cooler 31 may be necessary due to the concentration of R-32. The organic substances substantially free from HF is present at the bottom of the distillation apparatus, which is withdrawn as a bottom product stream 29.

On the other hand, the upper liquid phase rich in HF from the liquid phase separation apparatus 21 may be recycled to the reaction system, if possible. When not possible, another distillation apparatus is required. In FIG. 2, the upper liquid phase is supplied to the distillation apparatus 33 where it is separated into HF substantially free from the organic substances and the azeotropic mixtures of HF and the organic substances. Also in the distillation apparatus 33, a portion of the azeotropic mixture distillate of HF and the organic substances is returned to the top of the distillation apparatus as the reflux stream 37.

The balance is further cooled below a temperature of −200° C. through the cooler 41 and then returned to the liquid-liquid separation apparatus 21. HF stream 39 substantially free from the organic substances is re-used. Thus, all HF is effectively utilized while the organic substances are separated. The operation as described above may be carried out batch-wise, but preferably is carried out continuously.

EXAMPLES

The present invention will be, hereinafter, explained in detail with reference to Examples.

Example 1

HF (300 g, 15 mol) and R-30 (254.7 g, 3 mol) were charged in a previously evacuated distillation column made of stainless steel (diameter: 25 mm; packing: McMahon packing;

effective packing height: 1500 mm) and distillation was started with the total reflux operation while the temperature of the still was gradually increased. When the pressure of the column top was increased to 3.0 Kg/cm$^2$G and the temperature at the top was increased to 50° C., a sample was obtained from the reflux stream (which corresponds to the distillate liquid). The sample was analyzed and the molar ratio of HF/R-30 was 80/20.

It is clear from the above result that R-30 having a boiling point higher than that of HF (the boiling point at atmospheric pressure of HF is 19° C. which is lower than that of R-30 of 40° C.) was concentrated at the top of the column. This confirms the formation of the azeotropic mixture of HF and R-30.

Example 2

HF (20 g, 1 mol) and R-31 (548 g, 8 mol) were charged to the same evacuated column as in Example 1, and distillation was started with the total reflux operation while the temperature of the still was gradually increased.

When the pressure of the column top was increased to 5.8 Kg/cm$^2$G and the temperature at the top was increased to 40° C., a sample was obtained from the reflux liquid stream. The sample was analyzed and the molar ratio of HF/R-31 was 20/80.

It is clear from the above result that HF having a boiling point higher than that of R-31 (the boiling point at atmospheric pressure of R-31 is −9° C., which is lower than that of HF of 19° C.) was concentrated at the top of the column. This confirms the formation of the azeotropic mixture of HF and R-31.

Example 3

HF (2 g, 0.1 mol) and R-32 (520 g, 10 mol) were charged to the same evacuated column as in Example 1, and distillation was started with the total reflux operation while the temperature of the still was gradually increased. When the pressure of the column top was increased to 22 Kg/cm$^2$G and the temperature at the top was increased to 40° C., a sample was obtained from the reflux liquid stream. The sample was analyzed and a molar ratio of HF/R-32 was 1.2/98.8.

It is clear from the above result that HF having a boiling point higher than that of R-32 (the boiling point at atmospheric pressure of R-32 is −52° C. which is lower than that of HF of 19° C.) was concentrated at the top of the column. This confirms the formation of the azeotropic mixture of HF and R-32.

Example 4

To vapor-liquid equilibrium measuring apparatuses (volume 75 ml each) previously evacuated, mixtures (of about 60 g each) of HF and R-30, HF and R-31, and HF and R-32 each having the same composition as that of the sample (reflux) obtained in each of Examples 1 to 3 were charged, respectively. Then, the apparatus was heated such that the pressure of the system of the apparatus increased to 3.0, 5.8 and 22 Kg/cm$^2$G, respectively. After conditions of the system were in equilibrium, samples were obtained from the vapor phase and the liquid phase of each apparatus.

HF compositions of the vapor phase samples and the liquid phase samples are shown in below Table 1 below

TABLE 1

| Mixture | HF (mol %) in vapor | HF (mol %) in liquid | Pressure Kg/cm$^2$G | Temperature ° C. |
|---|---|---|---|---|
| HF & R-30 | 80 | 81 | 3.0 | 50 |
| HF & R-31 | 20 | 19 | 5.8 | 40 |
| HF & R-30 | 0.1 | 0.1 | 22 | 40 |

It is understood from the above results that the compositions of the vapor samples are equal to those of the liquid samples within experimental errors, which confirms that HF and R-30, HF and R-31, and HF and R-32 each forms an azeotropic mixture.

Example 5

HF (120 g, 6 mol) and R-30 (509.4 g, 6 mol) were charged to the same evacuated column as in Example 1, and distillation was started with the total reflux operation while the temperature of the still was gradually increased. When the pressure of the column top was increased to 3.0 Kg/cm$^2$G and the temperature at the top was increased to 50° C., a sample (of 2 g) was obtained from the reflux stream. The sample was analyzed and the molar ratio of HF/R-30 of the sample was 79.2/20.8.

Again, the still temperature was increased with the total reflux condition. When the pressure of the column top was increased to 15 Kg/cm$^2$G and the temperature at the top was increased to 112° C., a sample (of 2 g) was obtained from the reflux stream. The sample was analyzed and the molar ratio of HF/R-30 of the sample was 76.2/23.8. As seen from these results, the composition of the azeotropic mixture is slightly influenced by the system pressure.

Then, the pressure was returned to 3 Kg/cm$^2$G again, and the distillation column was stabilized. After being stabilized, when the distillate from the column top was gradually withdrawn outside the column, the top temperature of the column began to increase gradually. Then, when the top temperature was equal to the still temperature, heating of the column was stopped. The total amount of the distillate withdrawn from the column top was about 400 g (including the samples on the way), and about 220 g of R-30 was obtained from the still. Such R-30 contained about 10 ppm of HF.

Example 6

HF (10 g, 0.5 mol) and R-31 (548 g, 8 mol) were charged to the same evacuated column as in Example 1, and distillation was started with the total reflux operation while a temperature of the still was gradually increased. When the pressure of the column top was increased to 5.8 Kg/cm$^2$G and the temperature at the top was increased to 40° C., a sample (of 2 g) was obtained from the reflux stream. The sample was analyzed and the molar ratio of HF/R-31 of the sample was 20.2/79.8.

Again, the still temperature was increased with the total reflux condition. When the pressure of the column top was increased to 15 Kg/cm$^2$G and a temperature at the top was increased to 64° C., a sample (of 2 g) was obtained from the reflux stream. The sample was analyzed and a molar ratio of HF/R-31 of the sample was 19.5/80.5. As seen from these results, the composition of the azeotropic mixture is slightly influenced by the system pressure.

Then, the pressure was returned to 5.8 Kg/cm$^2$G again and the distillation column was stabilized. After being stabilized, when the distillate from the column top was gradually withdrawn outside the column, the top temperature of the column began to increase gradually. Then, when the top temperature was equal to the still temperature, heating of the column was stopped. A total amount of the distillate withdrawn from the column top was about 300 g (including the samples on the way), and about 250 g of R-31 was obtained from the still. Such R-31 contained about 13 ppm of HF.

Example 7

HF (0.05 g, 0.0025 mol) and R-32 (520 g, 10 mol) were charged to the same evacuated column as in Example 1, and distillation was started with the total reflux operation while a temperature of the still was gradually increased. When the pressure of the column top was increased to 22 Kg/cm$^2$G and the temperature at the top was increased to 40° C., a sample (of 2 g) was obtained from the reflux stream. The sample was analyzed and the molar ratio of HF/R-32 of the sample was 1.2/98.8.

Then, the still temperature was reduced with the total reflux condition. When the pressure of the column top was reduced to 15 Kg/cm$^2$G and the temperature at the top was reduced to 35° C., a sample (of 2 g) was obtained from the reflux stream. The sample was analyzed and a molar ratio of HF/R-32 of the sample was 1.2/98.8. As seen from this results, the composition of the azeotropic mixture is hardly influenced by the system pressure.

Then, the pressure was returned to 22 Kg/cm$^2$G again and the distillation column was stabilized. After being stabilized, when the distillate from the column top was gradually withdrawn outside the system, the top temperature of the column began to increase gradually. Then, when the top temperature was equal to the still temperature, heating of the column was stopped. The total amount of the distillate withdrawn from the column top was about 300 g (including the samples on the way), and about 210 g of R-32 was obtained from the still. Such R-32 contained about 30 ppm of HF.

Example 8

A mixture of HF, R-30, R-31 and R-32 was charged in the same evacuated apparatus as in that of Example 1, and the distillation operation was carried out. During the operation, samples were obtained from the reflux stream and the still liquid and analyzed. The compositions (unit: mol %) of the feed to the distillation column, the reflux stream and the still liquid each at the total reflux condition are shown in Table 2 in the case in which the molar ratio of R-31/HF of the mixture was 6, in Table 3 in the case in which the molar ratio was 2, and in Table 4 in the case in which the original molar ratio was 2 and then increased to 5 by the addition of R-31 to the feed.

TABLE 2

|  | Feed liquid | Reflux liquid | Still liquid |
|---|---|---|---|
| HF | 10 | 15 | trace |
| R-30 | 20 | trace | 56 |
| R-31 | 60 | 69 | 44 |
| R-32 | 10 | 16 | trace |
| Temperature (° C.) |  | 28 | 55 |
| Pressure (Kg/cm$^2$G) |  | 5 | 5 |

TABLE 3

|  | Feed liquid | Reflux liquid | Still liquid |
|---|---|---|---|
| HF | 20 | 19 | 22 |
| R-30 | 30 | trace | 78 |
| R-31 | 40 | 65 | trace |
| R-32 | 10 | 16 | trace |
| Temperature (° C.) |  | 28 | 68 |
| Pressure (Kg/cm$^2$G) |  | 5 | 5 |

TABLE 4

| | Feed | | Reflux | Still |
|---|---|---|---|---|
| | Original | After addition of R-31 | | |
| HF | 20 | 12.5 | 17 | trace |
| R-30 | 30 | 18.75 | trace | 72 |
| R-31 | 40 | 62.5 | 75 | 28 |
| R-32 | 10 | 6.25 | 8 | trace |
| Temperature (° C.) | | | 30 | 66 |
| Pressure (Kg/cm²G) | | | 5 | 5 |

On the basis of the above results, when the mixture of HF, R-30, R-31 and R-32 has the molar ratio of R-31/HF higher than 4, HF can be removed from the mixture.

Example 9

HF and R-30 were charged in a evacuated vessel made of a fluoroplastic in a HF/R-30 molar ratio of 50/50, then mixed and then left at a temperature of 20° C. so that the mixture was phase-separated. The HF/R-30 molar ratio of the lower liquid phase in such a separated condition was analyzed and it was 3/97. The HF/R-30 molar ratio of the upper liquid phase was 95/5.

Example 10

HF and R-31 were charged in the same evacuated apparatus as that of Example 9 in a HF/R-31 molar ratio of 50/50, then mixed and then left at a temperature of −40° C. so that the mixture was phase-separated. The HF/R-31 molar ratio of the lower liquid phase in such a separated condition was analyzed.

The HF/R-31 molar ratio was found to be 10/90. The HF/R-31 molar ratio of the upper liquid phase was 88/12.

Example 11

HF, R-30, R-31 and R-32 were charged in the same evacuated apparatus as that of Example 9 in a molar ratio of 50/20/20/10, respectively, then mixed and then left at a temperature of 0° C. so that it was phase-separated. The molar ratio of HF, R-30, R-31 and R-32 of the lower liquid phase in such a separated condition was analyzed and a HF/R-30/R-31/R-32 molar ratio was about 5/41/36/18. The HF/R-30/R-31/R-32 molar ratio of the upper liquid phase was about 91/1/5/3.

Example 12

HF, R-30, R-31 and R-32 were charged in the same evacuated apparatus as that of Example 9 in a molar ratio of 50/10/30/10, respectively, then mixed and then left at a temperature of 0° C. so that it was phase-separated. The molar ratio of HF, R-30, R-31 and R-32 of the lower liquid phase in such a separated condition was analyzed and the HF/R-30/R-31/R-32 molar ratio was about 9/21/53/17. This lower liquid mixture was subjected to a distillation operation by feeding it to the distillation column. The distillation was carried out with the total reflux condition and samples were obtained from the reflux stream and the still liquid and analyzed. The analysis results are shown below Table 5 (unit: mol %).

TABLE 5

| | Feed liquid | Reflux liquid | Still liquid |
|---|---|---|---|
| HF | 9 | 16 | trace |
| R-30 | 21 | trace | 50 |
| R-31 | 53 | 55 | 50 |
| R-32 | 17 | 29 | trace |
| Temperature (° C.) | | 25 | 52 |
| Pressure (Kg/cm²G) | | 5 | 5 |

Therefore, HF can be removed from the mixture of HF, R-30, R-31 and R-32 by the liquid separation and the distillation operations.

Example 13

A mixture of HF, R-30 and R-31 was charged in the same evacuated apparatus as that of Example 9 and then left at a temperature of 60° C. so that it was phase-separated. In such a separated condition, the molar ratio of HF, R-30 and R-31 of each of the upper liquid phase and the lower liquid phase was measured.

When the HF/R-30/R-31 molar ratio of the mixture was 76/8/16 and thus the R-30/R-31 molar ratio was 0.5, the liquid separation itself was observed. However, it was not possible to obtain a sample from the lower liquid phase and thus analysis could not be carried out. Results were shown in Table 6 (unit: mol %) which were obtained in the case where the molar ratio of the mixture was 76/12/12 and thus the R-30/R-31 molar ratio was 1.

TABLE 6

| | Feed liquid | Upper phase | Lower phase |
|---|---|---|---|
| HF | 76 | 82 | 9 |
| R-30 | 12 | 8 | 56 |
| R-31 | 12 | 10 | 35 |
| Temperature (° C.) | | 60 | 60 |
| Pressure (Kg/cm²G) | | 7.8 | 7.8 |

Therefore, the preferred embodiment of the present invention includes a process for the removal of HF which comprises steps of adding R-30 to a mixture comprising at least HF, R-30 and R-31 so that the R-30/R-31 molar ratio of the resulted mixture is increased above 0.5, cooling such a mixture below a temperature of 60° C. so that the mixture is separated into the upper liquid phase rich in HF and the lower liquid phase rich in R-30 and R-31, and recovering R-30 and R-31 from the lower liquid phase which contain less HF.

Example 14

A mixture of HF, R-30, R-31, and R-32 was charged in the same evacuated apparatus as in that of Example 9 and then left at a temperature of 60° C. so that it was phase-separated. In such a separated state, the molar ratio of HF, R-30, R-31 and R-32 of each of the upper liquid phase and the lower liquid phase was measured.

When the HF/R-30/R-31/R-32 molar ratio of the mixture was 70/9/18/3 and thus the molar ratio of R-30/R-31 was 0.5, the liquid separation itself was observed. However, it was not possible to obtain a sample from the lower liquid phase and thus analysis could not be carried out. Results were shown in Table 7 (unit: mol %) which were obtained in the case where the molar ratio of the mixture was 70/13.5/13.5/3 and thus the molar ratio of R-30/R-31 was 1.

TABLE 7

|  | Feed liquid | Upper phase | Lower phase |
|---|---|---|---|
| HF | 70 | 77 | 14 |
| R-30 | 13.5 | 9 | 47 |
| R-31 | 13.5 | 11 | 31 |
| R-32 | 3 | 2 | 7 |
| Temperature (° C.) |  | 60 | 60 |
| Pressure (Kg/cm$^2$G) |  | 9.8 | 9.8 |

Therefore, another preferred embodiment of the present invention includes a process for the removal of HF which comprises steps of adding a mixture of R-31 and R-30 or R-30 to a mixture comprising at least HF, R-30, R-31 and R-32 so that the R-30/R-31 molar ratio of the resulting mixture is increased above 0.5, cooling such a mixture below a temperature of 60° C. so that the mixture is separated into a upper liquid phase rich in HF and the lower liquid phase rich in R-32, R-31 and R-30, and recovering R-32, R-31 and R-30 from the lower liquid phase which contain less HF.

What is claimed is:

1. A process of removing hydrogen fluoride from a mixture of at least hydrogen fluoride and dichloromethane, which comprises distilling the mixture so as to remove hydrogen fluoride as an azeotropic mixture consisting essentially of hydrogen fluoride and dichloromethane.

2. The process according to claim 1, wherein a pressure during the distillation of the mixture is in the range of 0.5 Kg/cm$^2$-abs to 30 Kg/cm$^2$-abs, and a molar ratio of hydrogen fluoride to dichloromethane of the azeotropic mixture is about 80:20 at a pressure of 3.0 Kg/cm$^2$-G and about 77:23 at a pressure of 15 Kg/cm$^2$-G.

3. A process for reducing the amount of hydrogen fluoride from a first mixture of at least hydrogen fluoride, difluoromethane, chlorofluoromethane and dichloromethane which comprises:

distilling the first mixture so as to remove an azeotropic mixture of (1) hydrogen fluoride and (2) dichloromethane, chlorofluoromethane, or difluoromethane;

adding chlorofluoromethane to the first mixture when a molar ratio of chlorofluoromethane to hydrogen fluoride falls below four so as to form a second mixture with the molar ratio of chlorofluoromethane to hydrogen fluoride being higher than four; and distilling the second mixture so as to remove the azeotropic mixture.

4. The process according to claim 3 wherein a pressure during the distillation of the first and second mixtures is in the range of 0.5 Kg/cm$^2$-abs to 30 Kg/cm$^2$-abs.

* * * * *